United States Patent [19]

Doyle et al.

[11] Patent Number: 5,421,194
[45] Date of Patent: Jun. 6, 1995

[54] LIQUID QUALITY ANALYSIS SYSTEM COMBINING SPARGING AND AN INFRARED GAS CELL

[75] Inventors: Walter M. Doyle, Laguna Beach; Norman A. Jennings, Los Alamitos, both of Calif.

[73] Assignee: Axiom Analytical, Inc., Irvine, Calif.

[21] Appl. No.: 662,933

[22] Filed: Mar. 1, 1991

[51] Int. Cl.⁶ .......................................... G01N 11/00
[52] U.S. Cl. .................... 73/53.01; 73/19.01; 73/64.56
[58] Field of Search ............... 73/19.01, 19.1, 19.12, 73/61 R

[56] References Cited

U.S. PATENT DOCUMENTS

| | | | |
|---|---|---|---|
| 3,171,273 | 3/1965 | Dijkema | 73/19.1 |
| 3,673,853 | 7/1972 | Griswold et al. | 73/19.1 |
| 3,740,320 | 6/1973 | Arthur et al. | 73/19.01 |
| 3,942,792 | 3/1976 | Topol | 73/19.1 |
| 4,003,257 | 1/1977 | Fletcher et al. | 73/19.1 |
| 4,154,086 | 5/1979 | Button et al. | 73/19.1 |
| 4,314,969 | 2/1982 | Arthur et al. | 73/19.1 |
| 4,330,385 | 5/1982 | Arthur et al. | 73/19.1 |
| 4,528,635 | 7/1985 | Juodikis et al. | 73/61.77 |
| 4,599,217 | 7/1986 | Winston et al. | 73/866.4 |
| 4,681,601 | 7/1987 | Foster | 73/19.1 |
| 4,944,178 | 7/1990 | Inoue et al. | 73/19.1 |
| 5,062,292 | 11/1991 | Kanba et al. | 73/19.1 |

FOREIGN PATENT DOCUMENTS 0047531  2/1990  Japan .................. 73/19.01

Primary Examiner—Sandra L. O'Shea
Assistant Examiner—Raymond Y. Mah
Attorney, Agent, or Firm—Thomas J. Plante

[57] ABSTRACT

A sparging-infrared liquid analyzing system having a vessel in which a gas stream makes a single pass through a liquid stream containing contaminants, in order to provide vapor-to-liquid equilibrium of contaminants in the gas stream. The gas stream is then passed through a condenser, in which the gas temperature is precisely controlled, and the gas is cooled to a point below the dew point of water vapor in the gas stream. The gas is then flowed into a gas cell for infrared analysis. Water vapor effects are removed from the analytical output. Also, the effects of excessive depletion of relatively insoluble contaminants are removed from the analytical output.

4 Claims, 6 Drawing Sheets

LIQUID QUALITY ANALYSIS SYSTEM COMBINING SPARGING AND AN INFRARED GAS CELL

BACKGROUND OF THE INVENTION

This invention relates to improved techniques for analyzing (identifying and measuring) the concentrations of impurities in liquid, by using gas cell means to analyze vaporized molecules. Its primary purpose is to provide a rapid, continuous, substantially maintenance-free system for providing such analysis. Significant applications exist in such fields as the analysis of waste water discharged from chemical manufacturing plants.

The standard technique for measuring the concentrations of volatile substances in water is the "purge and trap" method. In that technique, an inert gas (typically nitrogen or ordinary air) is sparged (bubbled) through a volume of water and passed through a trap which collects the organics. The process is continued until essentially all of the organics are transferred to the trap. This takes typically 10 to 12 minutes. The trap is then back-flushed into a gas chromatograph (GC), which measures the various concentrations.

While the purge and trap method is widely used, it does have a number of deficiencies which make it undesirable for use as a continuous monitoring method in an industrial plant. For example: (a) an individual measurement may take from 20 to 30 minutes (at least 10 minutes for sparging and a comparable time for the GC analysis); (b) the process generally requires operator attendance; and (c) gas chromatography is a maintenance-intensive technique.

Unlike gas chromatography (GC), infrared (IR) spectroscopy can gather data on an almost continuous basis, and can perform a complete multicomponent analysis in a matter of seconds. This method thus offers the promise of rapid, low maintenance waste water analysis when used with a sparging system. However, implementing a practical sparging-IR system is not trivial. For one thing, the purge and trap method is no longer appropriate, since it defeats the fast response capability of the IR spectrometer. An alternative approach is to try to arrange a situation in which the vapor phase of each substance will be in equilibrium with its liquid phase solution in the incoming stream. At this point, the concentration of a given vapor in the gas stream will be a direct measure of the concentration of the corresponding liquid in solution. The gas stream can then be passed through an infrared gas cell for continuous analysis by an FTIR spectrometer.

A source of potential difficulty in a sparging-IR gas cell system is the fact that the concentration of water vapor in the gas stream will often be much higher than the concentrations of the organic vapors. One answer to this problem is to store a spectrum of pure water vapor, and then ratio the new measured spectrum against the stored spectrum, in order to cancel out the water spectrum. However, since the water vapor concentration can be quite high, small variations in its value can disrupt the measurement of the low levels of organics that are of interest. Such variations can arise from a change in the temperature of the water stream, or from a slight departure from equilibrium between the liquid water and its vapor.

At least one sparging-IR system has been developed, by the du Pont Corporation. The key elements of its system include the following. In the du Pont system, the waste water is sprayed through a volume of inert gas, rather than having the gas bubble through the liquid. The reason for this is concern about potential clogging of a gas sparging nozzle. Since the spray approach does not insure that all of the gas passing through the system will be saturated with the water vapor and organic vapors, the gas is circulated through the IR gas cell and then back through the extraction vessel on a continuous basis. After some number of passes (typically three), complete equilibrium will be achieved. Note that, although the gas is brought back into the extraction vessel below the water surface, the depth is arbitrary and no bubble forming nozzle is used. Water vapor interference is not a problem in the du Pont system, since the contaminants of interest to du Pont have absorption bands which do not overlap the water vapor bands. However, the system does use membrane type dryers to remove the possibility of water condensation in the IR gas cell.

In common with the du Pont system described above, the apparatus and method of the present application use an infrared (IR) spectrometer system as an on-line analyzer of contaminants in a waste water stream. However, substantial differences exist between the two systems.

SUMMARY OF THE INVENTION

The present invention provides a sparging-IR spectrometer system capable of applicability over a much wider range of contaminants, including those whose spectral bands (spikes in the spectrograph which identify various materials) overlap the spectral regions in which water vapor bands occur.

In order to provide background information accurately measuring the amount of water vapor, a condenser is used between the sparging vessel and the gas cell. The gas cell is the sample portion of a spectrometric analyzer. The temperature of the condenser is precisely controlled at a point significantly below the temperature of the waste water stream.

The condenser temperature is maintained below the dew point for the water vapor water vapor pressure, causing liquid water to condense out. The water vapor pressure in the post-condenser stream is equal to the equilibrium vapor pressure at the condenser temperature. The condenser will not affect the concentrations of the contaminant vapors in the stream since, for the low concentrations expected, the dew points of these vapors will be well below the temperature of the condenser.

The use of a temperature controlled condenser is beneficial in two ways. First, by precisely controlling the water vapor pressure, it enables the spectrometer to accurately ratio out the IR water vapor bands, independently of the temperature of the water stream. Second, the condenser temperature can be held at a relatively low point, so as to minimize the water vapor pressure, which decreases rapidly as the freezing point of water is approached. This substantially reduces the total amount of water vapor in the system.

Another aspect of the present invention is the operation of the sparging system at essentially atmospheric pressure, which avoids the possible problems of pressure build up in a closed loop system. The recirculating systems have the potential of developing pressure build up problems.

In the present invention, gas is bubbled through the waste water flow, using a sparging nozzle to produce very small bubbles. The depth of the water above the sparging nozzle is made sufficient so that the vapor pressure in each bubble reaches equilibrium with the liquid before the bubble reaches the surface. The required depth is dependent on the size of the bubbles and the volatility of the contaminants. Since all of the gas entering the system has to pass through the full depth of the liquid in the form of bubbles, it follows that all of the gas will contain contaminant vapors at their equilibrium vapor pressures.

A further aspect of the present invention is the use of increased liquid flow rates to prevent or reduce depletion of contaminants which are only slightly soluble, and are therefore likely to be inaccurately measured, if they are significantly depleted during the sparging process. Having a sufficiently high ratio of liquid flow rate to gas flow rate is useful in preventing contaminant depletion.

DETAILED DESCRIPTION OF PREFERRED EMBODIMENT

Figure 1:
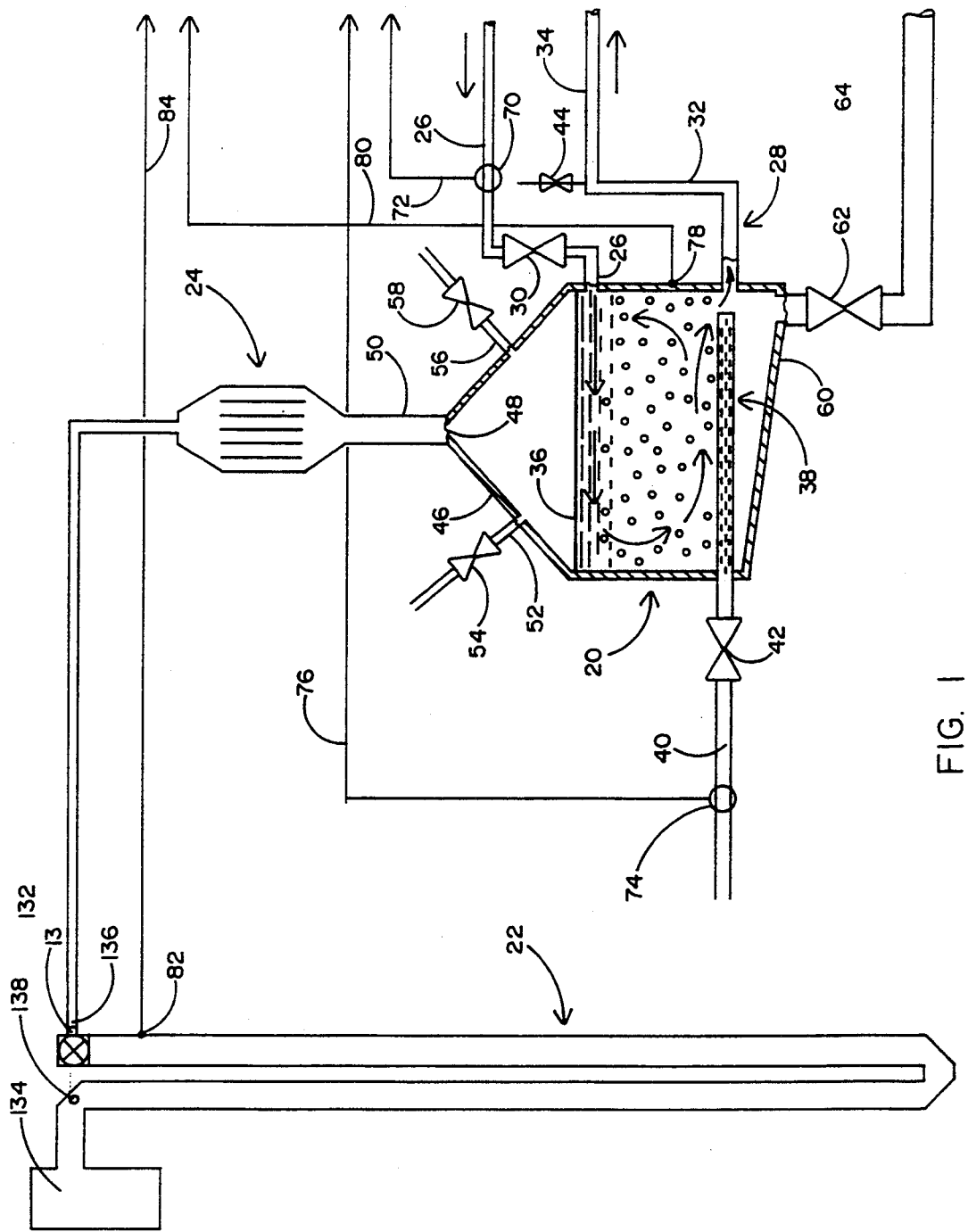
FIG. 1 is a schematic showing the elements of a sparging-IR system.

As shown in FIG. 1, an infrared analyzer using sparging means for maximizing gas/liquid contact includes a sparging vessel 20, a gas cell 22, and a condenser 24 connected between the outlet of the sparging vessel and the inlet of the gas cell.

The purpose of the sparging vessel 20 is to cause incoming gas bubbles to move through a stream of contaminated waste water, and extract therefrom vaporized contaminants contained in the water. The resulting gas is sent to a gas cell for analysis, in order to determine the amounts of various contaminants in the water.

The inflow of waste water enters vessel 20 through an inflow pipe 26 near the top of the water in the vessel. Water leaves vessel 20 through an outflow pipe 28 near the bottom of the vessel. A valve 30 is in pipe 26 to permit control of the incoming water flow. The outflow pipe 28 has a vertical portion 32 leading to a horizontal portion 34, the level of which determines the level of the top surface 36 of water in the vessel. The arrows in the figure indicate the desired circulating flow of water passing through vessel 20.

A sparging nozzle 38 extends into and across the bottom of the vessel 20. Gas, usually air, enters the sparging nozzle 38 from a pipe 40, through a control valve 42, and escapes from nozzle 38 through thousands (or millions) of tiny holes in the nozzle, thus forming bubbles, as shown in the figure. The bubbles, as they rise toward the surface 36 of the water, combine with vaporized contaminants in the water to provide a suitable gas for analysis in the gas cell 22.

The dimensions of the sparging vessel 20 are determined in part by the choice of sparging nozzle 38. A prototype uses a nozzle which is 12 inches long and ¾ inch in diameter. The horizontal cross-section of the prototype vessel 20 measures roughly 13 inches by 1.5 inches. As a result, air bubbles from the nozzle 38 will be generally uniformly distributed in the lower part of the vessel and will interact with all portions of the liquid volume as they rise to the surface. Because a sample of the waste water to be analyzed is brought into the vessel near the upper surface 36 of the water, and is withdrawn near the bottom of the same side, a circulating flow is created, with new water being directed across the top of the liquid. This means that, as the bubbles rise to the surface, the last layer of water they encounter will be new water that has experienced negligible depletion of contaminants.

As stated above, the output flow line 28/32/34 forms a trap that determines the level of liquid in the vessel. If the output is left open to the atmosphere, the liquid in the vessel will remain at the level of the output pipe. An antisiphon valve 44 is included, so that the liquid will remain at this level even if the output is connected to a closed drain line.

The depth of the liquid in vessel 20 is set at a sufficient level to achieve a saturated vapor pressure condition during a single pass of bubbles through the liquid. It has been learned that a water depth of about five inches is generally adequate for this purpose. The theoretical aspects of the dimensions and flow rates will be further discussed below.

The vessel 20 preferably has a tapered ceiling 46, at the apex of which is a gas orifice 48, through which rising gas enters an outlet pipe 50 connected to condenser 24. This gas outlet arrangement avoids dead volume, and encourages laminar flow of the gas from the surface of the liquid into the orifice 48. The upper portion of vessel 20 also has a clean water line 52 controlled by a valve 54, and a bypass gas inlet 56 controlled by a valve 58. These clean water and gas bypass lines 52 and 56 make it possible to take a reference spectrum either while sparging pure water or with only inert gas in gas cell 22.

The sparging vessel 20 includes a relatively large clean-out drain in the bottom of the vessel. This may be required for some applications,, in which the waste water contains a large amount of suspended particulate matter. During the sparging process, some of this matter may precipitate out to form a sludge in the bottom of the vessel. A sloped bottom surface 60 permits the sludge to accumulate in the bottom of the vessel. This sludge will be periodically cleaned out by opening a large drain valve 62 into drain pipe 64, and then flushing the system with a strong flow via the clean water inlet 52.

The bubbles entrained by the waste water stream provide a large air-liquid surface area for passage of dissolved volatile material (contaminants) into the gas phase of the analytical system. In the waste water stream, the contaminants to be measured are in liquid form. The sparging system is intended to rapidly reach equilibrium of the liquid and gas phases of the respective contaminants. Once such equilibrium is attained, measurement of the contaminant gasses in the gas cell permits measurement of the liquid contaminants in the waste water flow.

According to basic principles relating to vapor pressure and changes of state between liquid and gas, a liquid in a closed container will evaporate until equilibrium vapor pressure is attained. At equilibrium, the rate of condensation of gas molecules equals the rate of vaporation of liquid molecules. An equilibrium vapor pressure has been established. This equilibrium vapor pressure increases significantly with temperature increases; and it also increases with increased volatility of the liquid.

The contaminant materials in waste water from chemical processes generally have higher volatility than water. Such contaminants would eventually reach equilibrium vapor pressure by evaporation. However, excessive time would be required. Sparging tremendously increases the surface area of liquid to gas contact. The increase is many orders of magnitude, so that the gas-liquid equilibrium can be reached in a matter of seconds.

The system shown in FIG. 1 requires several sensors to provide volume and temperature information, which is directed to a computer (CPU) associated with the spectrometer. A liquid flow gauge 70 in inflow pipe 26 sends an electronic signal representing the liquid flow rate on line 72 to the CPU (not shown). A gas flow gauge 74 in gas pipe 40 sends an electronic signal representing the gas flow rate on line 76 to the CPU. A temperature sensor 78 in vessel 20 sends an electronic signal representing water temperature on line 80 to the CPU. A temperature sensor 82 in gas cell 22 sends an electronic signal representing gas temperature on line 84 to the CPU.

Figure 2:
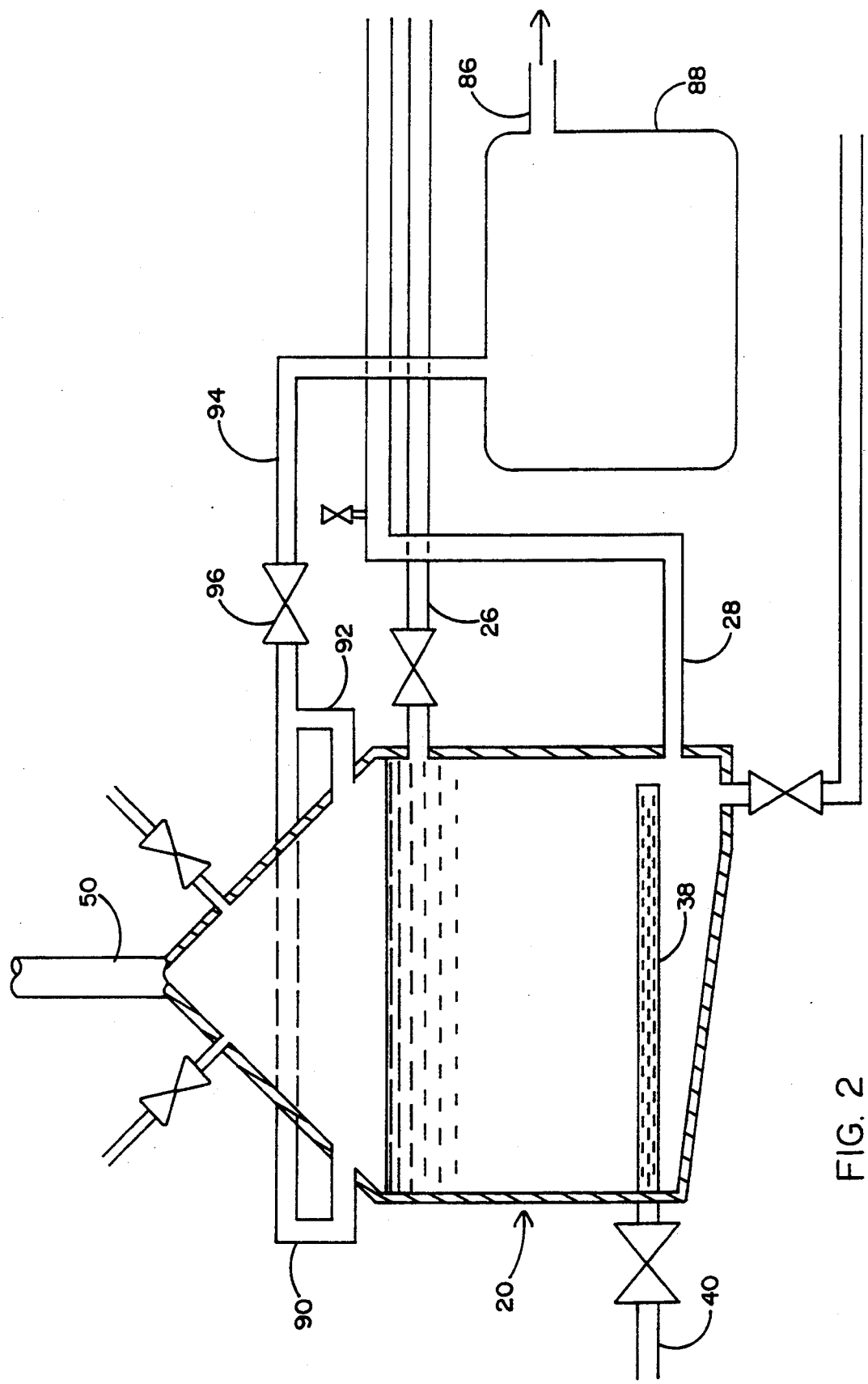
FIG. 2 is a schematic in which a clean-out tank is added to the sparging-IR system of FIG. 1.

FIG. 2 shows means for dealing with a problem that may occur in the sparging system. This is the formation of foam in the upper portion of vessel 20. As the foam builds up, it will be forced up into the condenser and eventually into the gas cell by the sparging air stream. This can interrupt the measurements and possibly damage the gas cell.

In FIG. 2, a foam-removing system uses a vacuum pump (not shown) which is connected to a gas pipe 86, leading from a holding tank 88. Two additional gas pipes 90 and 92 are connected to the air (gas) space in vessel 20 above the upper surface 36 of the liquid. Pipes 90 and 92 both connect to a pipe 94, which is opened and closed by a valve 96.

To use the foam clean-out :system, the flow of sparging gas in pipe 40 is turned off, and valve 96 is opened, permitting the vacuum pump to pump air backwards through the gas cell and down through the condenser, evacuating any foam from the system. This process can be made quite rapid by using tank 88 between the cleanout valve 96 and the vacuum pump. When the valve 96 is opened, the air and foam in the system are rapidly forced into tank 88.

Figure 4:
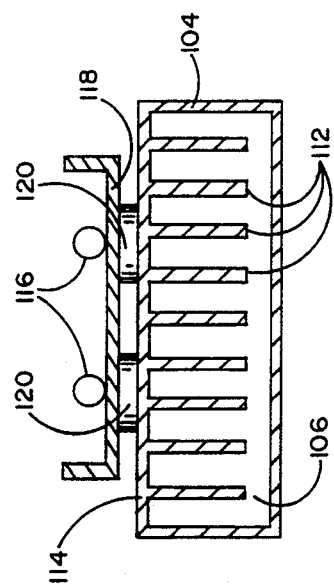
FIG. 4 is a section taken on line 4—4 of FIG. 3.
Figure 3:
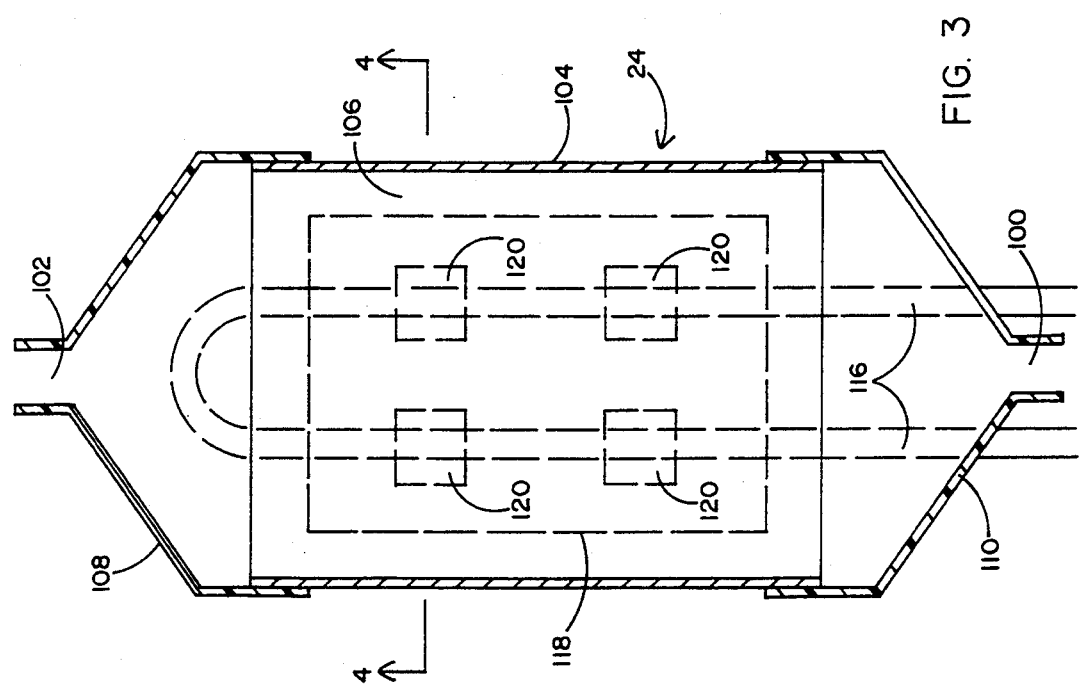
FIG. 3 is a sectional view through the condenser in the sparging-IR system.
Figure 5:
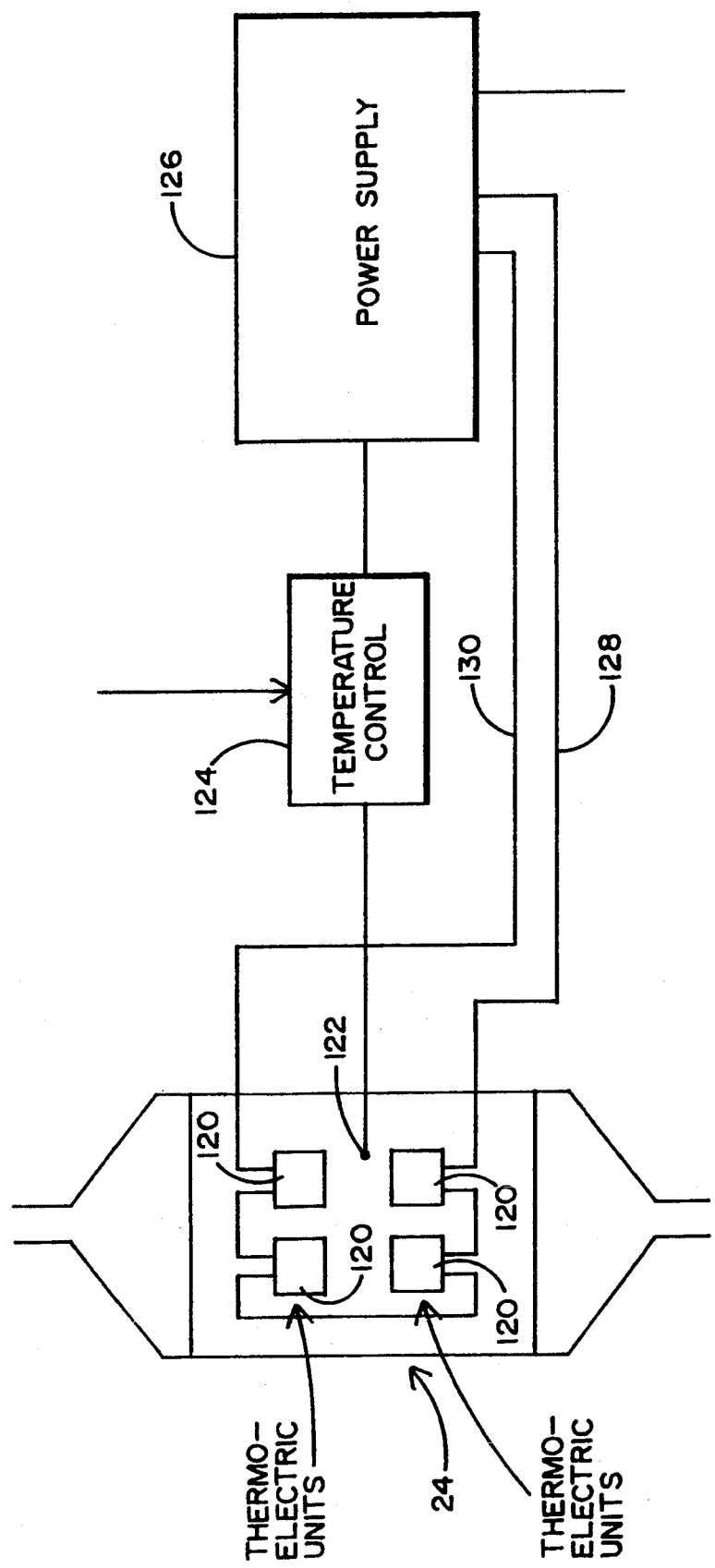
FIG. 5 is a schematic of the temperature control system of the condenser.

FIGS. 3, 4 and 5 show the structure and control system of the condenser 24 (FIG. 1). The purpose of the condenser is to maintain a precise water vapor pressure in the gas cell, so that the number of water vapor molecules per unit of gas volume in the gas cell is a fixed amount, which can be used in software calculations to remove the water vapor effect from the spectra produced by the gas cell (and the spectrometer system which includes the gas cell).

This maintenance of a known (and therefore, subtractable) water vapor factor in the gas being analyzed can be accomplished by having condenser 24 maintain a precise temperature a few degrees above freezing. The selected condenser temperature should be about 5° or 10° C. above freezing, so that it is below the dew point of the water vapor. Once the exact temperature of the condenser has been selected, it should be maintained within ±0.1° C., if possible. Probably the variation will be somewhat greater.

The gas from the sparging vessel 20 enters the condenser 24 through a bottom inlet 100, and exits from the condenser through a top outlet 102. The air travels through a metal housing 104 which provides a chamber 106 having a rectangular cross-section (FIG. 4). The upper and lower ends of the condenser may be closed by plastic caps 108 and 110, in which the gas outlet and inlet are formed.

As the gas rises in chamber 106, it is cooled by contact with a plurality of vertically-extending heatsink metal fins 112, which extend substantially across chamber 102, and which carry heat extracted from the gas to the back wall 114 of chamber 106.

The cooling system may comprise a U-shaped water pipe 116, which engages a metal heat-conducting plate 118; and a plurality of Peltier (thermoelectric) units 120. Four Peltier units are shown, mounted between, and in engagement with, the gas-warmed wall 114, and the water cooled plate 118.

FIG. 5 shows the temperature control system of the condenser. A temperature sensor 122 has an electrical lead to a temperature controller 124, at which a manually operable temperature adjustment member is provided. Controller 124 sends electrical signals to a voltage-controllable power supply 126. Power supply 126 is connected to the four Peltier units 120, which are wired in series. One line 128 runs between the power supply 126 and the first Peltier unit, and another line 130 runs between the power supply 126 and the fourth Peltier unit.

If the temperature sensor 122 shows a temperature higher than that set at controller 124, a signal to the power supply 126 causes it to increase the voltage on the Peltier units, thereby causing a reduction in the temperature. If the temperature sensor 122 shows a temperature lower than that set at controller 124, a signal to the power supply 126 causes it to decrease the voltage on the Peltier units, thereby causing an increase in the temperature.

Since the condenser temperature is typically thirty or forty degrees cooler than the waste water stream, and the water vapor is already nearly saturated at the water temperature, liquid water will .drip back from the condenser into the sparging vessel, leaving water vapor in equilibrium with the liquid phase at the condenser temperature. Since this is precisely controlled, the water vapor pressure will not change and, in fact, will remain constant as the gas passes through the gas cell and out of the system. Note that the total gas pressure will be approximately one atmosphere, since the flow path is open to the air at the output of the gas cell. One benefit of leaving the output of gas flow open to atmospheric pressure rather than recirculating it with an air pump is that this insures a constant pressure and hence constant water vapor absorbtion in the gas cell.

The gas cell 22 (FIG. 1) is preferably a laminar flow, light pipe cell of the type disclosed in application Ser. No. 487,619, filed Mar. 2, 1990, now U.S. Pat. No. 5,065,025 and assigned to the assignee of this application. The low purge volume and resultant fast response time of that gas cell is especially important for the present sparging-IR system. One prototype uses a two meter long gas cell. However, gas cells ranging from one to eight meters long will probably prove useful for various applications.

In FIG. 1, the infrared radiation of the spectrometer (not shown) is shown entering gas pipe 22 at 132. An infrared detector 134 receives the infrared radiation after it has travelled through the length of the gas cell 22. The gas cell from condenser 24 enters the gas cell at 136 and exits at 138.

The contaminants in a waste water stream have solubilities ranging from highly soluble to almost insoluble. For relatively soluble contaminants, a situation can be readily reached in which the solute in the waste water stream is in equilibrium with its vapor in the sparging gas stream. It is important that this equilibrium be reached without substantially depleting the amount of contaminant in the water stream, in order to obtain accurate data concerning the contaminant concentration.

Adjustments of the water flow rate and the gas flow rate are useful in controlling the length of time needed to reach vapor-to-liquid equilibrium, and the amount of depletion that occurs once equilibrium is reached. Increases in the water flow rate are useful in reaching vapor-to-liquid equilibrium before significant contaminant depletion occurs in the water stream.

The condition of reaching equilibrium with negligible depletion can be attained only if the rate of depletion of the solute by the sparging gas is low enough to allow the measurement to be made before appreciable depletion of the solute takes place. In a practical situation, the water stream is flowing. The flow rate must be adequate to insure that negligible solute depletion takes place during the time that a given volume of water is in the vessel. In the case of solutes having an extremely low solubility, the concentration might be depleted significantly during the sparging process for any practical combination of air and water flow rates.

Figure 6:
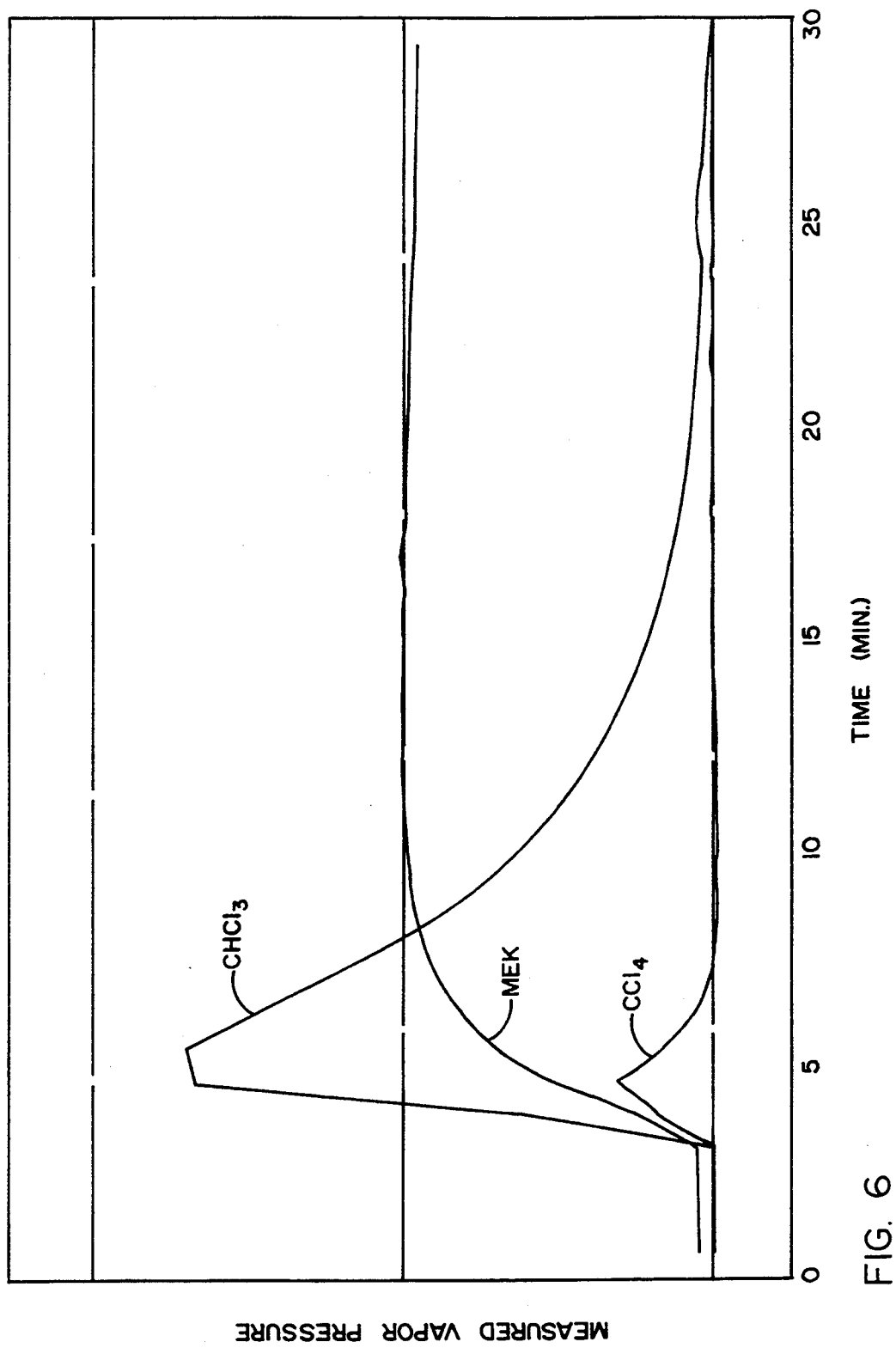
FIG. 6 is a graph which plots measured vapor pressure against elapsed time for three common contaminant materials.

FIG. 6 shows experimentally measured concentration curves for three different solutes using the herein disclosed sparging IR system in the static mode (i.e., no water flow). The rise time of the signal in each case depends on the volume in the gaseous portion of the system (i.e., the upper part of the sparging vessel 20, the condenser 24 and the gas cell 22). The rise time is the time required to purge the system of gas already present and to fill the gas cell with gas that has been sparged through the waste water. This time is minimized to the extent that the flow in the system is laminar.

FIG. 6 includes curves representing three substances: methyl ethyl ketone (MEK), chloroform (CHCl$_3$) and carbon tetrachloride (CCl$_4$). In FIG. 6, the X-axis numbers represent time in minutes. The Y-axis represents the gas cell measured vapor pressure. The lack of smoothness in the curves in the figure is due to relatively slow time resolution of the software used in the experiment. The results shown in the figure were obtained with a static water supply. The initial time lag is the time needed to purge the stale air in the system.

MEK is a highly soluble substance. With this material, the rise time is very fast compared to the solute depletion time. If the vessel is sufficiently deep, a measurement is obtained which is independent of depth, gas flow rate, and water flow rate—i.e., a direct measure of the concentration. The leveling point of the MEK curve represents the time when the stale air has been purged.

In the case of CHCl$_3$, the depletion time appears to be about 4 times the rise time. This is fast enough to lead to some depletion of the solute before a measurement can be made, at least in the static measurement mode. However, it is reasonable to expect that the waste water can be replenished fast enough so that depletion due to sparging would not have a significant affect on the gas cell measurement.

In the case of CCl$_4$, the depletion time is about 1.5 times the rise time. Even in this case, it is likely that the water can be replenished fast enough to minimize the effect of depletion. Nevertheless, there will be some substances for which it will not be possible to achieve a high enough ratio of water flow rate to air flow rate, since at some point a large percentage of the air bubbles would be swept out with the water stream. However, maximizing the water to air flow rate will minimize the dependence of the measurement on these parameters.

A significant advantage of the sparging-IR technique is its sensitivity, due to the fact that vapor pressure of a given contaminant is not directly proportional to the fractional concentration of that contaminant (incorrectly taught in many chemistry text books).

Assume a volume of air in equilibrium with a volume of water containing a small amount of a chemical having a low solubility in water. The concentration of solute vapor in the air will be proportional to the fractional saturation of the solute in the water. For example, if the saturation concentration of the solute is one part per million, then a concentration of one half part per million in water will result in a partial pressure in the air volume equal to one half the normal saturated vapor pressure of the pure substance.

The ideal gas law states that a quantity of gaseous material equal to "n" in moles will occupy a volume equal to:

$V_g = RTn/P$ (liters); where $R=0.08206$; $T=$temperature (Kelvin); and $P=$pressure (Atmospheres).

Now consider a small amount of the same substance dissolved in water. The total volume of liquid solute dissolved in the water will be given by $V_s = F_s S V_w d_w/d_s$; where $V_w=$water volume; $S=$solubility (gm/gm); $F_s=$fractional saturation; $d_w=$specific gravity of water (1 gm/ml); and $d_s=$specific gravity of solute.

If this solution is allowed to come to equilibrium with a very small air volume, the partial pressure of solute in the air will be equal to $P_f = F_s P_s$; where $P_s$ is the vapor pressure of the pure substance at the appropriate temperature.

Now consider a situation in which the solution is exposed to a closed volume of air just large enough so that equilibrium between the liquid and the gas phase is reached after one half of the dissolve solute has evaporated into the air volume. At this point, the partial pressure will be one half of the value obtained for a very small air volume, i.e., $P = 0.5\ P_f = 0.5\ F_s P_s$ Call the gas volume that gives rise to this amount of depletion the "half-depletion" volume. At this point, the total number of moles of the solute in the gas phase will be:

$n = 0.5\ V_s d_s/w = 0.5\ F_s S V_w/W$; where $W=$molecular weight.

Returning to the ideal gas law, and using it to determine the half depletion volume by substituting the expressions for P and n given above, gives the following:

$V_h = RTn/P = RT (S/P_sW)V_w$.

At room temperature $RT = 24,600$ ml, Atm/mol.

From the above, it follows that the half depletion volume is independent of the initial fractional saturation of the solute, depending only on the water volume and on the fixed physical constants of the material. Using these constants, the ratio of $V_h$ to $V_w$ can be calculated for various materials of interest. Some examples are:

Methyl ethyl ketone $V_h/V_w = 4860$
Methylene chloride $V_h/V_w = 12.6$
Chloroform $V_h/V_w = 7.9$
Benzene $V_h/V_w = 2.2$ Some other materials of interest, such as $CCl_4$, are listed in the handbooks as being insoluble in water. However, these materials actually are slightly soluble. A reasonable guess might be that the half depletion volume ratio for $CCl_4$ is in the range of 1.0 to 3.0.

The above analysis demonstrates that the depletion process is exponential. This permits calculating the amount of depletion for a given air flow volume passing through a given volume of water. For example, for an actual volume ratio equal to 1/5 of the half depletion ratio, the amount of depletion will be about 13%. In other words, there will be an error of about 13% if a measurement is made without taking into consideration the effects of depletion.

In actual operation, both the air and the water will be flowing. It is appropriate, in this case, to interpret "volume" in the volume ratio expressions as flow volume per unit time. Thus, in order to insure that the measurement is reasonably independent of the actual flow rates, the ratio of volume flow rates should be no greater than, say, 1/5 of the half depletion ratio calculated for the substance being analyzed. For materials having very low solubility, it may not be practical to achieve the required flow ratio. In such cases, it will be necessary to measure the actual flow rates, and to use these measurements in conjunction with an appropriate calibration to obtain the actual concentration.

Since the treatment given above is only approximately correct for the flowing case, it would be desirable to test the predictions against experimental measurements for materials having known physical properties. In cases where the solubility is unknown, the sparging IR process can be used in the static mode to measure its value.

Figure 7:
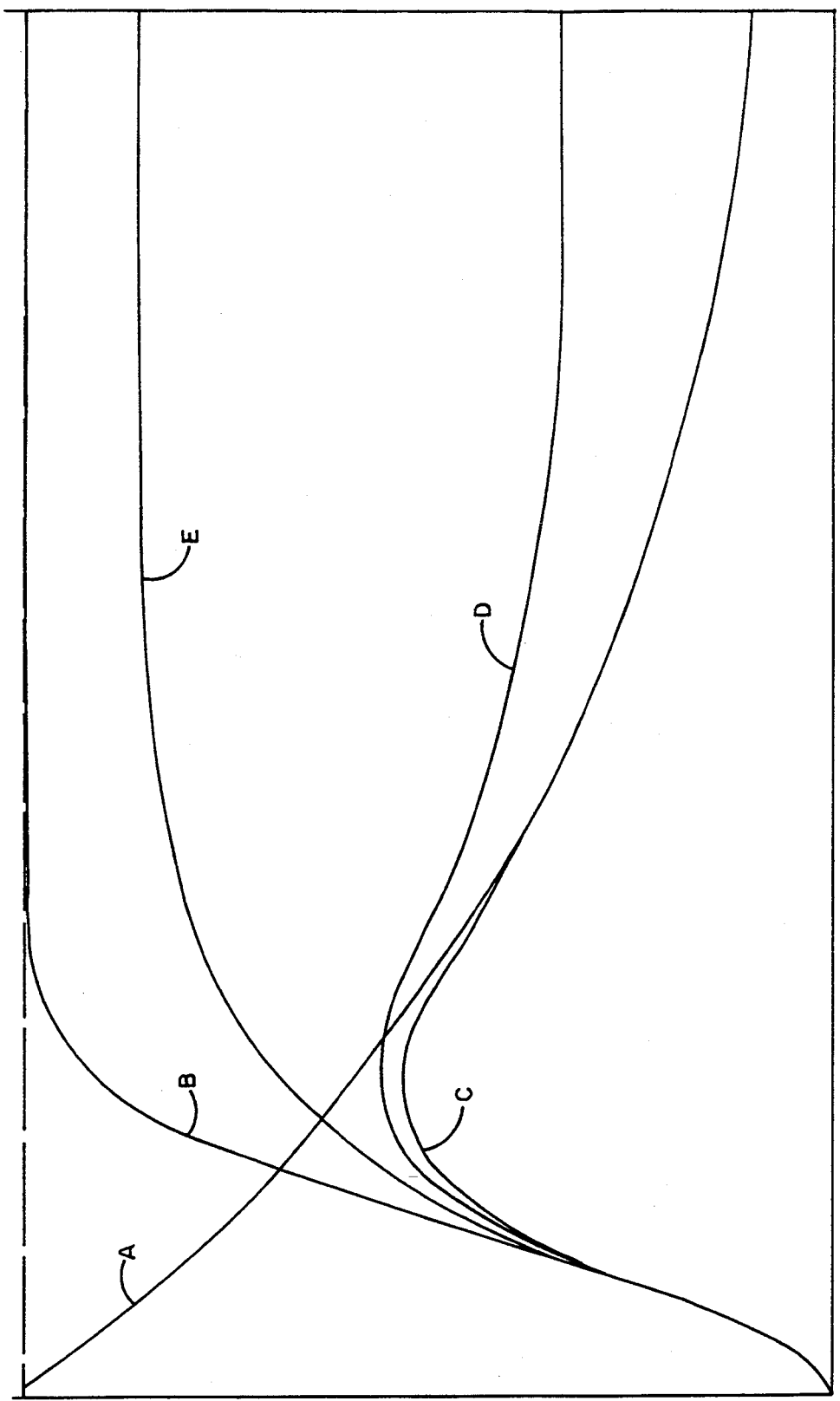
FIG. 7 is a graph showing the same variables as FIG. 6, and curves which illustrate the principles involved in maintaining low contaminant depletion.

The various considerations discussed above can be understood with reference to FIG. 7. Here, curve A represents the static case (no water flow) in which the volume of the gas cell is small compared to the liquid volume. The measured vapor pressure simply decays exponentially as the solute is sparged out of the water. Curve B corresponds to the case in which the air to water volume ratio is very small compared to the half depletion ratio, i.e., either the solute is highly soluble or the water flow rate is very high. The rise time is determined simply by the time required to purge out the air in the system and replace it with sparged air and solute vapor. Curve C corresponds to a static measurement in which the half depletion volume is comparable to the volume of the gas cell and the associated plumbing. Finally, curves D and E represent practical situations involving the same solute as curve C, but with two different water flow velocities. As the water velocity is increased (from curve D to E), the departure from the ideal case (curve B) is minimized.

This demonstrates that even relatively insoluble materials may be analyzed by the herein disclosed system.

In such cases, the water flow rate would be increased as much as possible. And calculations of the amount of depletion would be used to modify the analytical information produced by the gas cell. Such calculations would rely on experimentally determined values.

In other words, there are three ways to get reliable data: (1) increasing the water flow rate so that depletion is minimal; (2) calibrating the system for flow based on experiments to determine how the measurement is dependent on flow; and (3) taking the data just as it stands and extrapolating backwards, i.e., mathematically determining what the concentration is by looking at the shape of the curves.

From the foregoing description it is apparent that the herein disclosed apparatus and method provide at least three important benefits:

(1) Fast response to changes in the composition of the liquid stream;

(2) Lack of sensitivity to water vapor interference; and (3) High accuracy by reaching equilibrium in a single pass of the liquid and gas streams, and by avoidance of miscalculations due to contaminant depletion.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A process for detecting and measuring contaminants in a flowing liquid stream, comprising:
   causing the liquid stream to enter, flow through and then exit from a vessel;
   causing a gas stream to enter the vessel and flow upwardly through the liquid in the form of bubbles;
   directing the gas stream to a gas cell in which the contaminants will be identified and measured;
   cooling the gas stream between the vessel and the gas cell, in order to provide a known water vapor effect, by passing the gas stream through a condenser which brings it to a predetermined constant temperature below the dew point of water vapor;
   controlling the condenser temperature within $\pm 1°$ Centigrade;
   calibrating the process experimentally for one or more selected contaminants under a range of flow conditions spanning those to be used analytically;
   adjusting the analytical data from the gas cell to compensate for the depletion experienced at the flow rate used; and
   compensating for the water vapor effect in the information supplied by the gas cell.

2. A process for detecting and measuring contaminants in a flowing liquid stream, comprising:
   causing the liquid stream to enter, flow through and then exit from a vessel;
   causing a gas stream to enter the vessel and flow upwardly through the liquid in the form of bubbles;
   directing the gas stream to a gas cell in which the contaminants will be identified and measured;
   calibrating the process experimentally for one or more selected contaminants under a range of flow conditions spanning those to be used analytically;

said calibration incorporating calculation of the amount of depletion of the contaminant(s) as a function of time; and adjusting the analytical data from the gas cell to compensate for the depletion experienced at the flow rate used.

3. A process for detecting and measuring contaminants in a flowing liquid stream, comprising;

causing the liquid stream to enter, flow through and then exit from a vessel;

causing a gas stream to enter the vessel and flow upwardly through the liquid in the form of closely spaced bubbles;

controlling the temperature of the gas entering the gas cell to within ±1° Centigrade;

adjusting the depth of the liquid to the vessel so that the vapor and liquid forms of one or more contaminants will reach equilibrium; and directing the gas stream to a gas cell in which the contaminants will be identified and measured.

4. A process for detecting and measuring contaminants in a flowing liquid stream, comprising;

causing the liquid stream to enter, flow through and then exit from a vessel;

causing a gas stream to enter the vessel and flow upwardly through the liquid in the form of closely spaced bubbles;

causing the ratio of the rate of gas flow to the rate of liquid flow to be no more than one-third of a half depletion volume ratio;

adjusting the depth of the liquid to the vessel so that the vapor and liquid forms of one or more contaminants will reach equilibrium; and directing the gas stream to a gas cell in which the contaminants will be identified and measured.

* * * * *